United States Patent [19]
Russell et al.

[11] Patent Number: 5,478,910
[45] Date of Patent: Dec. 26, 1995

[54] PROCESS FOR THE PRODUCTION OF POLYESTERS USING ENZYMES AND SUPERCRITICAL FLUIDS

[75] Inventors: Alan J. Russell, Wexford; Eric J. Beckman, Edgewood; Diaf Abderrahmare; Apurva K. Chaudhary, both of Pittsburgh, all of Pa.

[73] Assignee: Bayer Corporation, Pittsburgh, Pa.

[21] Appl. No.: 397,326

[22] Filed: Mar. 1, 1995

[51] Int. Cl.$^6$ .................................................. C08G 63/82
[52] U.S. Cl. ........................ 528/274; 528/272; 528/483; 524/700; 435/183
[58] Field of Search .................................. 528/272, 274, 528/483; 524/700; 435/183

[56] References Cited

PUBLICATIONS

Morrow, MRS Bulletin, Nov. 1992, pp. 43–47.
Geresh et al, Biotechnology and Bioengineering, vol. 36, 1190 (Month Unavailable) pp. 270–274.
Morrow et al, Mat. Res. Soc. Symp. Proc., vol. 174, 1990, (Month Unavailable) pp. 197–208.
Wallace et al, J. Poly. Sci.: Part A: Poly. Chem., vol. 27, (Month unavailable) 1989 pp. 2553–2567 and pp. 3271–3284.
Margolin et al, Tetrahedron Let., vol. 28, No. 15, 1987, pp. 1607–1610.
Binns et al, J. Chem. Soc. Perkin Trans, 1, (Month unavailable) 1993 pp. 899–904.
Knani et al, J. Poly. Sci.: Part A: Poly. Chem., vol. 31 (Month unavailable) 1983, pp. 1221–1232 and pp. 2887–2897.
Athawale et al, Biotechnologies Let., vol. 16, No. 2, Feb., 1994, pp. 149–154.
Williams, Chem. Eng. Sci., vol. 36, No. 11, 1981, pp. 1769–1788 (Month unavailable).
Paulaitis et al, Rev. Chem. Eng., vol. 1, No. 2, 1983 (Month Unavailable) pp. 179–250 (pp. 234, 235, 248 and 249 are missing).
Halling, Enzyme Microb. Tech., Mar. 1994, vol. 16, pp. 178–206.
Randolph et al, Biocatal. Ind., (Month Unavailable) 1985, vol. 7, No. 5, pp. 219–237.
Randolph et al, Biocatal. Ind. (Month Unavailable) 1991, Chapter 11, pp. 325–328.
Aaltonen et al, Chemtech, Apr. 1991, vol. 224, pp. 240–248.
Perrut, High Pressure and Biotech., (Month Unavailable) 1992, vol. 224 pp. 401–410.
Shen et al, Biocatal. in Non–Conventional Media, (Month Unavailable) 1992, pp. 417–423.
Russell et al, Applied Biochem and Biotech., vol. 31, (Month Unavailable) 1991, pp. 197–211.
J. Am. Chem. Soc., (Month Unavailable) 1993, vol. 115, No. 19, pp. 8845 and 8846.
Russell et al. in Chemtech, Mar. 1994, pp. 33–37.

*Primary Examiner*—Samuel A. Acquah
*Attorney, Agent, or Firm*—Joseph C. Gil

[57] ABSTRACT

A process of preparing a polyester by reacting a diol with an acid or acid ester in the presence of a solid enzyme and in a supercritical fluid is described.

10 Claims, No Drawings

PROCESS FOR THE PRODUCTION OF POLYESTERS USING ENZYMES AND SUPERCRITICAL FLUIDS

BACKGROUND OF THE INVENTION

Enzymes are known for their ability to selectively catalyze reactions in both aqueous and non-aqueous media. There is a growing interest in the biocatalytic synthesis of specialty polymers since such an approach can generate additional properties such as chirality and biodegradability. Biologically synthesized polymers have been applied as absorbents, biodegradable materials, chiral adsorbents, liquid crystals, and perm-selective membranes. The enzymatic synthesis of oligoesters and polyesters is known and is described, e.g. in Morrow, MRS Bulletin, Nov. 1992, pages 43–47; Geresh et al, Biotechnology and Bioengineering, Vol. 36, 1990, pages 270–274; Morrow et al, Mat. Res. Soc. Symp. Proc., vol. 174, 1990, pages 197–208; Wallace et al, J. Poly. Sci.: Part A: Poly. Chem., Vol 27, 1989, pages 2553–2567 and pages 3271–3284; Margolin et al, Tetrahedron Let., Vol. 28, No. 15, 1987, pages 1607–1610; Binns et al, J. Chem. Soc. Perkin Trans, 1, 1993, pages 899–904; Knani et al, J.Poly. Sci.: Part A: Poly. Chem., Vol 31, 1993, pages 1221–1232 and pages 2887–2897; and, Athawale et al, Biotechnologies Let., Vol. 16, no. 2, Feb., 1994, pages 149–154.

Low molecular weight linear aliphatic oligoesters which are hydroxy terminated have commercial significance for use in the manufacture of polyurethane resins. The current commercial process is based on acid/base catalyzed condensation polymerization between a diacid/diester and a diol. The use of traditional catalysts is limited because such catalysts tend to have an undesirable effect on the subsequent polyurethane synthesis.

Supercritical fluids have been described as extraction solvents and have been used in various industrial extraction processes (see, e.g., Chem. Eng. Sci., Vol. 36, no.11, 1981, pages 1769–1788; and Paulaitis et al, Rev. Chem. Eng., Vol. 1, No. 2, 1983, pages 179–250). Supercritical fluids have also been suggested as being useful for a variety of enzyme catalyzed reactions (see, e.g., Hailing, Enzyme Microb. Tech., March 1994, vol.16, pages 178–206; Randolph et al, Biotech. Let., vol. 7, no. 5, 1985, pages 325–328; Randolph et al, Biocatal. Ind., 1991, Chapter 11, pages 219–237; Aaltonen et al, Chemtech, April 1991, pages 240–248; Perrut, High Pressure and Biotech., 1992, Vol. 224, pages 401–410; Shen et al, Biocatal. in Non-Conventional Media, 1992, pages 417–323; Russell et al, Applied Biochem and Biotech., Vol. 31, 1191, pages 197–211). With supercritical fluids as the reaction medium, enzyme enantioselectivity can be manipulated by the pressure of the system. (see Kamat et al, J. Am. Chem.Soc., 1993, Vol. 115, No. 19, pages 8845–8846). Certain of the work which formed the basis of the present application was described by Russell et al in Chemtech, March 1994, pages 33–37.

In both enzymatic and non-enzyme catalyzed synthesis of oligoesters and polyesters, it is difficult to control product molecular weight in a predictable manner. All techniques described to date depend upon changing the reaction time in order to manipulate molecular weight. In the case of non-enzyme catalyzed oligo- and polyesters, the final product typically contains cyclic ester by-products and small amounts of residual catalyst, both of which can adversely affect properties of products produced from those oligo- and polyesters.

DESCRIPTION OF THE INVENTION

The present invention overcomes the above described difficulties and allows for the production of a wide variety of polyesters where it is relatively simple to produce a material of a desired molecular weight by merely varying the pressure under which the polyesterification or polytransesterification reaction is conducted.

More particularly, the present invention is directed to a process for producing a polyester comprising reacting an organic diol with either an organic diester or an organic dicarboxylic acid in the presence of a supercritical fluid and in the presence of a solid esterase (and preferably a lipase) enzyme, said process being conducted at a temperature of 20° C. or less, preferably at a temperature of from 20° to 80° C. and at a pressure of 100 psi or more, and preferably at a pressure of from 1000 to 5000 psi, with the proviso that the temperature of reaction satisfies the following formula:

$$0.85 \leq T/T_c \leq 1.2,$$

where T is the temperature, in °K, at which the process is conducted, and $T_c$ is the critical temperature, in °K, of the particular supercritical fluid used.

The $T/T_c$ ratio is preferably from 0.9 to 1.1.

The organic diols useful herein are known. Such diols generally range in molecular weight from as low as 60 to as high as about 200, and preferably have molecular weights of from 62 to about 150. The following are examples of suitable diols: ethylene glycol; propylene glycol-(1,2) and -(1,3); butylene glycol-(1,4) and -(2,3); hexanediol and its various isomers; octanediol and its various isomers; neopentylglycol; cyclohexanedimethanol (1,4-bis-hydroxymethyl-cyclohexane); 2-methyl-1,3-propane-diol; diethylene glycol, triethylene glycol, tetraethylene glycol and polyethylene glycols; dipropylene glycol and polypropylene glycols; and dibutylene glycol and polybutylene glycols.

The organic dicarboxylic acids useful herein are also known. Instead of the free dicarboxylic acids, the corresponding acid diesters of lower alcohols or mixtures thereof may be used for preparing the polyesters herein. The polycarboxylic acids may be aliphatic, cycloaliphatic, aromatic and/or heterocyclic and they may be substituted, e.g. by halogen atoms, and/or may be unsaturated. The following are mentioned as examples: succinic acid, adipic acid, suberic acid, azelaic acid, sebacic acid, phthalic acid, isophthalic acid, trimellitic acid, maleic acid, fumaric acid, dimeric and trimeric fatty acids, dimethyl terephthalic and terephthalic acid-bis-glycol esters. When used herein, the term "acid" is also intended to cover the corresponding anhydrides. Such anhydrides include phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid anhydride, and the like.

The diesters useful herein are prepared by art-recognized techniques. For example they can be prepared by reacting the particular diacid with a sufficient amount of monoalcohol to react with both carboxylic acid groups. Specifically preferred diesters are divinyl adipate, bis(2,2,2-trichloroethyl) adipate, bis(2,2,2-trifluoroethyl) adipate, and diallyl adipate.

The amounts of ester/acid to diol used are such that the COOR:OH (where R is either H in the case of an acid or the residue of the alcohol used to prepare the ester) equivalent ratio is from 1:2 to 2:1, and preferably from 1:1 to 1:1.2. In the most preferred embodiment a 1:1 ratio is used.

The solid esterase enzymes useful herein are also known and are available. The preferred enzymes used herein are lipase enzymes which have an Enzyme Commission number of 3.1.1.3. Specific useful enzymes include the following (unless otherwise indicated the enzymes listed have E.C. nos. of 3.1.1.3):

a) Available from Sigma Chemical Company:

Candida Cylindracea Lipase L-1754

Subtilisin Carlesberg Protease P-5380 (E.C. no. 3.4.4.16)

PPL (L-3082 and L-3126)

b) Available from Novo Nordisk:

the various Lipozyme products

Novozyme No435

SP-523

SP-525

SP-526

The amount of solid esterase used can vary over a wide range and is typically at least 0.01% by weight, based upon the total weight of diol, ester/acid and enzyme. The upper limit is dictated primarily by economic considerations, since the cost of producing the product will increase as the amount of catalyst increases. Usually, the level of catalyst used would go no higher than about 65% by weight. It is preferred that the amount of catalyst range from 0.01 to 10% by weight based upon the total weight of diol, ester/acid and enzyme.

Supercritical fluids are known. As is known, a supercritical fluid is a material above its critical temperature and critical pressure. Under such conditions the material attains physical characteristics between those of a gas and a liquid. Substantially any gas which has a critical temperature below 120° C. and a critical pressure below 3,000 psi would be a suitable material for use herein. Specific materials which are suitable for use as supercritical fluids include carbon dioxide, sulfur hexafluoride, xenon, ethane, ethylene, fluoroform (Freon 23) and Freon 13. The amount of supercritical fluid used is dictated by the volume of the particular reaction vessel used and is substantially equal to the volume of the reaction vessel. The weight of supercritical fluid will be pressure and volume dependent at a given temperature since supercritical fluids are compressible.

In preparing the polyesters of the present invention, the components are first charged to a suitable reactor which is then sealed and pressurized with the supercritical fluid. The reactor is heated to a suitable temperature and the components are allowed to react for an appropriate time depending upon the amount of esterase used (the more enzyme, the shorter the reaction time needed). The reaction mixture is preferably stirred. Typically, the time of reaction is no more than 120 hours, although longer times may be desired and/or necessary.

The products of the present invention are characterized by weight average molecular weights, as determined by GPC analysis, of from about 100 to about 10,000, preferably from 250 to 6,000, and most preferably from 400 to 4,000. In the present invention, the average molecular weight of a particular product is dependent upon the pressure of reaction. The esters produced herein typically contain from 3 to 50 repeating ester units. In addition, the products have polydispersity indices of from about 1.0 to 4.0, and preferably from 1.02 to 3.5. The polydispersity index ("PDI") is determined by dividing the weight average molecular weight by the number average molecular weight. The number average molecular weight is also determined from GPC analysis. PDI is essentially a measure of the breadth of the molecular weight distribution in a polymer sample. The closer the PDI is to 1.0, the tighter (or narrower) is the distribution. Commercial polyesters used in the polyurethane industry typically have PDIs of above 3.0.

The invention is further illustrated but is not intended to be limited by the following examples in which all parts and percentages are by weight unless otherwise specified.

EXAMPLES

In the examples, the following materials were used:

N-435: Novozyme 435, a commercially available triacylglycerol hydrolase (E.C. number 3.1.1.3), form Novo Nordisk BD: 1,4-butane diol DVA: divinyladipate TCEA: bis( 2,2,2-trichloroethyl )adipate THF: tetrahydrofuran DEG: diethylene glycol NPG: neopentyl glycol L-3126: a commercially available porcine pancreatic lipase (E.C. number 3.1.1.3) from Sigma Chemical Co.

Example 1

In Example 1, N-435 was used for the enzymatic catalysis for the polycondensation of DVA with BD in supercritical fluoroform (freon 23). 0.594 g of DVA, 0.270 g of BD and 1.2 g of N-435 (dried under reduced pressure for 3 days at room temperature) were placed in a high pressure stainless steel reactor (30 mL volumetric capacity) equipped with a magnetic stirring system. The reactor was sealed and then pressurized with fluoroform via an automated syringe pump. Heating of the reactor was provided by electric heating bands installed around the core of the reactor. The polymerization reaction was allowed to proceed for 3 days at 1600 psig and 50° C. After venting the reactor, 15 mL of THF were added to the reactor to solubilize the polymer. Molecular weight determination by GPC showed Mw=3260 with a PDI=3.70. End group analysis by NMR showed that the polymer was all dihydroxy capped.

Example 2

Example 1 was repeated using supercritical carbon dioxide ($CO_2$) in place of supercritical fluoroform. GPC analysis of the solubilized polymer showed an Mw of 200.

Example 3

Example 1 was repeated substituting 0.285 g of DEG for the BD. GPC analysis of the solubilized product showed an Mw of 1961 and a PDI of 2.50.

Example 4

Example 1 was repeated substituting 0.312 g of NPG for the BD. GPC analysis of the solubilized product showed an Mw of 900 and a PDI of 3.42. The GPC diagram also showed a small shoulder in the 2000 molecular range.

Example 5

Example 1 was repeated substituting 0.80 g of L3126 for the N-435. GPC analysis of the solubilized product showed an Mw of 700 and a PDI of 2.87. The GPC diagram also showed a small shoulder in the 2000 molecular range.

Example 6

L-3126 was used for the enzymatic catalysis for the polycondensation of TCEA with BD in supercritical fluoroform (freon 23). 3.10 g of TCEA, 0.68 g of BD and 0.80 g of L-3126 (dried under reduced pressure for 3 days at room temperature) were placed in a high pressure stainless steel reactor (30 mL volumetric capacity) equipped with a magnetic stirring system. The reactor was sealed and then pressurized with fluoroform via an automated syringe pump. Heating of the reactor was provided by electric heating bands installed around the core of the reactor. The polymerization reaction was allowed to proceed for 120 hours at various pressures and 50° C. After venting the reactor, 15 mL of THF were added to the reactor to solubilize the polymer. Molecular weight determination by GPC showed the following:

TABLE

| Reaction Pressure | Mw | PDI |
|---|---|---|
| 900 | 937 | 1.07 |
| 1600 | 1037 | 1.11 |
| 2400 | 1371 | 1.18 |
| 3000 | 1762 | 1.23 |

Example 7

Example 6 was repeated. Instead of THF addition at the end of the reaction, the product of each reaction was rinsed with fluoroform at the reaction temperature using a Hewlett Packard HP 7680A supercritical fluid extractor operated at 50° C. and pressures equal to the reaction pressure (except for the product produced at 900 psig, where the rinsing was conducted at the 1200 psig minimum pressure of operation of the extractor). For product produced at 900 psig, Mw of the precipitated fraction was 764 and PDI was 1.02. Similarly for product produced at 1600 psig, Mw was 1272 and PDI was 1.03. For product produced at 2400 psig, Mw was 2130 and PDI was 1.03, and for product produced at 3000 psig, Mw was 2590 and PDI was 1.05. NMR analysis of end groups showed that the polymers were all hydroxy-capped.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a polyester comprising reacting an organic diol with either an organic diester or an organic dicarboxylic acid in the presence of a supercritical fluid and in the presence of a solid esterase enzyme, said process being conducted at a temperature of 120° C. or less and at a pressure of 100 psi or more, with the proviso that the temperature of reaction satisfies the following formula:

$$0.85 \leq T/T_c \leq 1.2,$$

where T is the temperature, in °K, at which the process is conducted,
and
$T_c$ is the critical temperature, in °K, of the particular supercritical fluid used.

2. The process of claim 1 conducted at a temperature of from 20° to 80° C. and a pressure of from 1000 to 5000 psi.

3. The process of claim 1, wherein the organic diol has a molecular weight of from about 60 to about 200.

4. The process of claim 1, wherein the amounts of diol and either diester or acid used are such that the carboxylic group (ester) to hydroxyl group equivalent ratio is from 1:2 to 2:1.

5. The process of claim 1, wherein said ratio is from 1:1 to 1.2.

6. The process of claim 1, wherein the amount of said enzyme is at least 0.01% by weight, based upon the total weight of diol, diester or diacid and enzyme, and wherein said enzyme has an Enzyme Commission number of 3.1.1.3.

7. The process of claim 1, wherein the amount of said enzyme is from 0.01 to 10% by weight.

8. The process of claim 1, wherein said polyester contains from 3 to 50 repeating ester units.

9. The process of claim 1, wherein said polyester has a polydispersity index of from 1.02 to 3.5.

10. The process of claim 1, wherein $T/T_c$ is from 0.9 to 1.1.

* * * * *